(12) United States Patent
Berger et al.

(10) Patent No.: US 8,408,072 B2
(45) Date of Patent: Apr. 2, 2013

(54) COUPLING ELEMENT FOR AN ULTRASONIC FLOW MEASURING DEVICE

(75) Inventors: Andreas Berger, Therwil (CH); Quirin Muller, Basel (CH); Achim Wiest, Weil Am Rhein (DE)

(73) Assignee: Endress + Hauser Flowtec AG, Reinach (CH)

( * ) Notice: Subject to any disclaimer, the term of this patent is extended or adjusted under 35 U.S.C. 154(b) by 424 days.

(21) Appl. No.: 12/733,049

(22) PCT Filed: Jul. 10, 2008

(86) PCT No.: PCT/EP2008/058968
§ 371 (c)(1),
(2), (4) Date: May 18, 2010

(87) PCT Pub. No.: WO2009/024403
PCT Pub. Date: Feb. 26, 2009

(65) Prior Publication Data
US 2011/0239780 A1    Oct. 6, 2011

(30) Foreign Application Priority Data
Aug. 17, 2007  (DE) .......................... 10 2007 039 016

(51) Int. Cl.
*G01F 1/66* (2006.01)

(52) U.S. Cl. .................................. 73/861.28
(58) Field of Classification Search ... 73/861.25–861.28
See application file for complete search history.

(56) References Cited

U.S. PATENT DOCUMENTS

| 5,463,905 | A  | * | 11/1995 | Baird ........................ | 73/861.25 |
| 7,412,902 | B2 | * | 8/2008  | Wiest et al. ............... | 73/861.25 |
| 7,469,599 | B2 | * | 12/2008 | Froehlich et al. .......... | 73/861.27 |
| 7,523,677 | B2 | * | 4/2009  | Wiest et al. ............... | 73/861.27 |
| 7,703,337 | B1 | * | 4/2010  | Feller ........................ | 73/861.27 |
| 8,047,081 | B2 | * | 11/2011 | Berberig et al. .......... | 73/861.25 |
| 2004/0095045 | A1 |  | 5/2004  | Baumbartner |  |

FOREIGN PATENT DOCUMENTS

| DE | 31 36 797 | 5/1982 |
| DE | 41 24 692 | 1/1993 |
| DE | 101 33 395 | 1/2003 |
| DE | 10 2007 010 500 A1 | 9/2008 |
| EP | 0 198 731 A2 | 10/1986 |
| EP | 0 974 814 | 1/2000 |
| EP | 1 840 530 A2 | 10/2007 |
| GB | 2 086 183 | 5/1982 |

* cited by examiner

Primary Examiner — Jewel V Thompson
(74) Attorney, Agent, or Firm — Bacon & Thomas, PLLC (57) ABSTRACT

A coupling element for an ultrasonic, flow measuring device, wherein the coupling element has a pedestal with a bearing surface, on which bearing surface a piezoelement is applied. The pedestal is an integral component of the coupling element.

8 Claims, 6 Drawing Sheets

COUPLING ELEMENT FOR AN ULTRASONIC FLOW MEASURING DEVICE

TECHNICAL FIELD

The present invention relates to a coupling element for an ultrasonic, flow measuring device.

BACKGROUND DISCUSSION

Ultrasonic, flow measuring devices are widely used in process and automation technology. They allow, in a simple manner, contactless ascertaining of volume flow in a pipeline.

Known ultrasonic, flow measuring devices work frequently according to the Doppler principle or according to the travel-time difference principle.

In the case of the travel-time difference principle, the different travel times of ultrasonic pulses relative to the flow direction of the liquid are evaluated.

For this, the ultrasonic pulses are sent both in the direction of flow, as well as opposite to the direction of flow. From the travel-time difference, the flow velocity and, therewith, in the case of the known diameter of the pipeline section, the volume flow, e.g. volume flow rate, can be determined.

In the case of the Doppler principle, ultrasonic waves of a certain frequency are coupled into the liquid and the ultrasonic waves reflected from the liquid are evaluated. From the frequency shift between the injected and reflected waves, the flow velocity of the liquid can likewise be determined.

Reflections occur in the liquid, however, only if small air bubbles or impurities are present, so that this principle is mainly used for contaminated liquids.

The ultrasonic waves are generated and, respectively, received with the help of so-called ultrasonic transducers. For this, the ultrasonic transducer is placed securely on the pipe wall of the relevant section of pipeline. More recently, clamp-on ultrasonic flow measuring systems are available. With these systems, the ultrasonic transducers are only pressed against the tube wall with a clamp. Such systems are known e.g. from European Patent 686 255, U.S. Pat. Nos. 4,484,478 or 4,598,593.

Another type of ultrasonic, flow measuring device, which operates according to the travel-time difference principle, is described in U.S. Pat. No. 5,052,230. Here, the travel time is ascertained by means of bursts in the form of short, sinusoidal, ultrasonic pulses.

Ultrasonic transducers are typically composed of a piezoelectric element, also called a piezo for short, and a coupling element, also called a coupling wedge or, less frequently, a lead-in element, which is made of plastic. The ultrasonic waves are generated in the piezoelectric element and conveyed via the coupling element to the tube wall and from there into the liquid. Since sound velocities are different in liquids and plastics, the ultrasonic waves are refracted when passing from one medium to another. The angle of refraction is determined by Snell's law. Thus, the angle of refraction is dependent on the ratio of the propagation velocities in the two media.

From the state of the art, electrical contacting of piezoelectric elements is known to technically qualified persons. The electric contacts are located on the side of the piezoelement opposite to the flatly mounted side. The piezoelectric element has electrically conductive coatings on both sides and the coating on the fixedly mounted side extends to the opposite side of the piezoelectric element, where it can be contacted. This leads to the fact that the electrically conductive coating on the side opposite the flatly mounted side covers only part of the surface. Thus only a portion of the piezo surface is used.

Conventional coupling elements are manufactured of plastic and have a bore, ih which the piezoelectric element is applied. For manufacturing reasons, this application is burdened by tolerances. For instance, a non-uniform distribution of the adhesive can occur, whereby the piezoelectric element assumes an undefined spacing from the coupling element. Furthermore, the placement of the piezoelectric element in the bore of the coupling element has tolerance issues, such that the position of the area of sound emergence varies from sensor to sensor. The manufacture of a piezoelectric element and therewith the size of the area of sound emergence of the sensor is itself subject to certain tolerances. The sum of these tolerances results in measurement error.

Typically, a sensor holder is oriented on the pipe and correspondingly secured and the coupling element is oriented in the sensor holder. As a result, manufacturing related tolerances of individual, assembled components add to the error in the position of the piezo relative to the pipeline wall, or relative to the measured medium and/or relative to an additional sensor or its piezoelectric element of the measuring system. In order to keep these errors small, the individual components have to be formed by complicated and expensive processes.

As a result of the described construction, usually high mechanical stresses occur on the piezoelectric element. These stresses arise from thermal expansion or the mechanical attachment of the sensor to a pipeline and are transmitted via the walls of the coupling element.

SUMMARY OF THE INVENTION

An object of the invention is to provide a cost effectively manufactured sensor of compact construction for an ultrasonic, flow measuring device.

The object is achieved by features including that the coupling element has a pedestal with a bearing surface, on which is applied a piezoelectric element, and that the coupling element with pedestal is manufactured from one piece. The pedestal is, thus, an integral component of the coupling element. A sensor of the invention is cost effective to manufacture and has a compact construction. Due to the few components and the associated lower overall tolerances, this sensor, and, thus, the measuring system, measures very exactly.

An essential idea of the invention is that a piezoelectric element is firmly attached to the piezoelectric element facing area of the pedestal of the coupling element by means of an adhesive layer. Therebetween, in the usual way, an adapting, or matching, layer can be applied. The piezoelectric element facing area of the pedestal or the adapting layer may be referred to as the adhering surface. The coupling element with the pedestal is manufactured from one piece. Because of the free space between the pedestal and the outer surfaces and the inner wall of the coupling element, mechanical stresses in the sensor, e.g. from the securing of the sensor by means of a screw or from temperature fluctuations, are only transferred to the piezoelectric element to a small extent. The functioning of the piezoelectric element remains uninfluenced thereby. An additional basic idea of the invention lies in the use of very few components. There arises, thus, a smaller ultrasonic sensor with few components.

In an advantageous further development of the apparatus of the invention, the one piece coupling element is manufactured, or finally worked, in a jig, so that all functional surfaces are defined with very small tolerances in their manufacture and shape, especially in their orientation relative to each other. The apparatus of the invention is particularly advantageous for application for flow measuring systems based on ultrasound. An ultrasonic sensor of the invention can be applied for all conceivable tube diameters and can assume a corresponding size. For tubes with a nominal diameter of about 50 mm, for example, the pedestal height (PH) can be about 1 to 3 mm. When attaching the piezoelectric element, the adhesives should not flow to the pedestal base. Adhesives, which flow from the pedestal to the pedestal base could act as an acoustic and/or mechanical, connecting bridge and thus transmit acoustic signals and/or mechanical stresses to the piezo. The coupling element can be produced, for example, by machining or by casting.

An additive embodiment of the apparatus of the invention provides that sufficiently wide radii are provided on the pedestal base, in order to avoid, as much as possible, stress concentrations, and therewith, cracks in the material. These radii must be adjusted as a function of material and use conditions (e.g. temperature). An adapting, or matching, layer, preferably a disk, especially of a material, such as e.g. glass and/or aluminum is to be applied on the pedestal in such a manner that the free surface of the adapting, or matching, layer forms the adhering surface for the applying of the piezoelement. The thermal expansion coefficient of such matching layers lies, most often, between that of the coupling element and that of the piezoelement.

An advantageous embodiment of the apparatus of the invention provides that the piezoelement, which is applied on the pedestal of the coupling element, protrudes beyond the bearing surface of the pedestal. The area of the piezoelement, which is secured to the pedestal, is greater than the area of the pedestal, on which the piezoelement is secured, and, therewith, the piezoelement extends beyond the edge of the pedestal, especially the piezoelement extends beyond all sides of the pedestal. In this embodiment, position and area of sound emergence are exactly known. The manufacturing accuracy of the pedestal lies according to standard in the region of $1/100$ mm. In comparison, the piezoelement has a standard tolerance of $1/10$ to $2/10$ mm. To manufacture the piezoelement likewise in the $1/100$ mm-region would require an enormous extra cost. To apply a piezoelement to an area with a tolerance in the region of $1/100$ mm would require a highly accurate and very complicated and therewith costly technology. In the case of mounting the apparatus of the invention, this is not necessary, since the piezo is permitted to extend beyond the sides of the pedestal differently far. The area of sound emergence is defined, according to the invention, via the pedestal surface.

Another advantageous embodiment of the apparatus of the invention provides that the pedestal has a tub shaped recess with a surrounding rim and a tub floor, wherein the area of the rim facing the piezoelement forms the bearing surface for the piezoelement, wherein the bearing surface has a height HU relative to the tub floor and wherein the tub shaped recess is filled at least partially with adhesive. The tub floor forms, thus, the adhering surface. However, also here, an adapting, or matching, layer can be applied on, or in, the tub floor. The piezoelement lies on the rim, thus on the tub edges. The tub is filled with adhesive up to the height of the rim, thus up to the height of the pedestal HP, before the piezoelement is applied. The adhesive loses, in the case of the drying, or curing, process little or no mass, i.e. it contracts, or shrinks, according to the invention, very little or not at all, so that the piezoelement is drawn only very little or not at all into the tub and in such case is deformed only slightly or not at all.

According to a very advantageous form of embodiment of the apparatus of the invention, the adhesive layer has the same thickness over approximately its entire area and extends parallel to the piezo. An exact definition of the adhesive layer is possible on the basis of the tub of the pedestal, e.g. with overflow. In this way, an exactly defined adhesive quantity and its distribution is determined.

In an advantageous form of embodiment of the apparatus of the invention, it is provided, that the coupling element has guiding elements, which are distributed around the pedestal. The guiding elements have approximately equal distances D to the pedestal and approximately equal heights HN, wherein HN is greater than the height HP of the bearing surface of the pedestal. In such case, the guiding elements are resiliently seated, or very elastic, e.g. as thin as possible, so that their influence on the sound field is approximately zero. The ultrasound is according to the invention only transmitted via the pedestal in the perpendicular direction from the flatly applied piezoelement. The guiding elements have manufacturing, or mounting, advantages. Advantageously, they are formed out of the coupling element and are thus an integral component thereof. Further advantageously, they are exchangeably embodied, e.g. pins removable after the mounting process, which are emplaced in pin holes provided therefor. Alternatively, also guiding noses can be provided.

An advantageous form of embodiment of the apparatus of the invention includes features that the piezoelement is electrically contacted both on the side facing the pedestal, as well as also on the side facing away from the pedestal, over, in each case, approximately the entire area, especially that a braided wire, or wires with an approximately equal thickness, are arranged between the piezoelement and the bearing surface and/or between the piezoelement and the tub floor of the pedestal. Concerning the braided wire, it can also be represented by an individual wire or a number of individual wires. It is arranged between the piezoelement and the adhering surface of the pedestal. This braided wire is composed preferably of electrically conductive material and is connected with the piezoelement fixedly and/or electrically conductively. By the projecting of the piezo beyond the bearing surface and/or by the application of the braided wire, an option is to contact the two sides of the piezo directly and, thus, to utilize the entire area of the piezo. Additionally, the braided wire in the tub of the pedestal serves as spacer between piezo and tub floor, or adhering surface. Alternatively to the tub of the pedestal formed by means of the rim, the braided wire can lie on a flat bearing surface of the pedestal and serve itself to form a tub for defined applying of the adhesive. At the same time, the aforementioned tasks of spacer and electrical contacting of the piezo are retained.

A very advantageous embodiment of the apparatus of the invention is that in which the coupling element has at least one other functional surface, by means of which a sensor holder is oriented relative to the coupling element and/or by means of which the coupling element is oriented on or with respect to a pipeline, in which the medium to be measured flows. According to the invention, the coupling element itself is oriented on the pipeline, in which the medium to be measured flows. A base of the coupling element is provided, which serves as a functional surface for orientation, and which is manufactured in a clamp or jig along with the manufacturing of the applying, or adhering, surface for mounting the piezo. The angle and the location of the piezo relative to outer surfaces and other bodies of the measuring system, especially relative to the pipeline and to the measured medium, are, corresponding to the small tolerances, exactly determined.

Especially advantageously, supplementally to the base of the coupling element, the area, e.g. on the pipe, on which the coupling element is oriented, is correspondingly prepared. For securement of the oriented coupling element, as other functional surfaces, e.g. a securement bore or an installation geometry are provided in the coupling element for a pressure piece.

Representing another functional surface of the coupling element is the area for the application of the sensor holder. Thus, the position of the sensor holder around the coupling element is exactly defined, corresponding to the small manufacturing tolerances, especially with determined, according to the invention, very little, influence on the sound field and therewith on the measuring. This arrangement of the functional surfaces is especially suitable for clamp-on ultrasonic measuring devices. In the case of built-in sensors, the sensor holder serves for orientation of the coupling element relative to the pipeline. Most often, the sensor holder is in such case connected with the pipeline by material bond. Through corresponding working of the sensor holder, the sound emergence surface can, corresponding to the small manufacturing tolerances, likewise be exactly positioned, e.g. relative to the measured medium.

Another very advantageous embodiment of the apparatus of the invention lies in the fact that the coupling element has at least one other functional surface, by means of which an anti-kink device for the connection cable, which serves as a passageway seal for the connection cable, is oriented on the coupling element. The anti-kink device is applied simply and accurately positioned on the coupling element by means of the functional surface. Especially advantageously, the anti-kink device is injected onto the coupling element as a potting compound, whereby components and working steps are saved.

Another very advantageous embodiment of the apparatus of the invention provides that the coupling element has at least one other functional surface, by means of which a connecting circuit board is oriented on the coupling element.

A supplementing embodiment of the apparatus of the invention provides that two sensors, which are placed on the pipeline, in which the medium to be measured flows, belong to a measuring system, wherein the contacting of the piezoelement is performed on the, in each case, other side of the two piezoelements. This is especially of advantage in the case of sensors, which are placed on the same side of the pipeline, in which the medium to be measured flows, thus belonging to a measuring system, which utilizes the oppositely lying pipeline wall as a reflection body.

A variant of the apparatus of the invention is that wherein a cavity is provided in the pedestal for contacting the piezoelement and/or a larger piezo projection is provided on a certain side of the pedestal for contacting the piezoelement.

Another variant of the apparatus of the invention provides that an overflow is provided in the rim of the pedestal, in order that the adhesive layer possesses an exactly defined thickness. Through this overflow, a wire can be guided, which belongs to the braided wire lying in the tub, which is provided e.g. for contacting the piezoelement.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
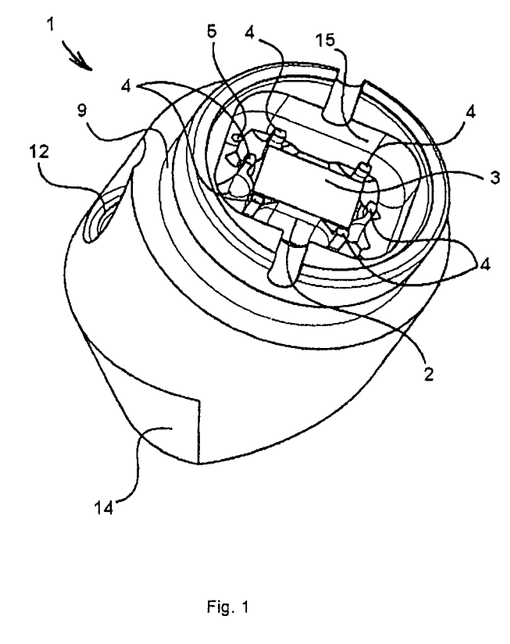
FIG. 1 shows, perspectively, a coupling element of the invention for an ultrasonic, flow measuring device.

FIG. 1 shows, perspectively, a coupling element 1 with a pedestal 2. The pedestal 2 is an integral component of the coupling element 1. The pedestal 2 is not only of the same material as the coupling element 1, a high temperature thermoplastic, and is connected with this by material bond, e.g. by an adhesive connection, but, also, the coupling element 1 is, with the pedestal 2, manufactured from one body, so-to-say made from a solid piece.

The pedestal 2 includes a bearing surface 3, on which the piezoelement 19 (not shown in FIG. 1) is applied. The bearing surface 3 is in this drawing simultaneously the adhering surface, whereon the adhesive layer is applied. Alternatively, there can be applied on the bearing surface 3 an adapting, or matching, layer 20 (not shown in FIG. 1) or an adapting, or matching, layer is set into the bearing surface, so that the adapting, or matching, layer 20 forms the adhering surface.

Besides the bearing surface 3, the pedestal 2 has guiding elements 4, which extend up from the bearing surface 3. The guiding elements 4 are very elastic or resiliently seated and function as mounting aids in the manufacture, or mounting, of the piezoelement. In this example of an embodiment, the guiding elements 4 are integrated into the pedestal 2. Alternatively, they can be emplaced alongside the pedestal 2. Besides the illustrated guiding elements 4, pin holes for accommodating removable pins for the positioning, or mounting, of the piezoelement are another option, by which the guiding elements 4, as described, can be replaced.

Additionally, the coupling element 1 has a pin hole 5, which is provided for accommodating a solder pin 6 (not shown in FIG. 1). This serves for contacting the piezoelement. Alternatively, there can be applied on the bearing surface 3 of the pedestal 2 a braided wire, which serves for contacting the piezoelement 19 and simultaneously forms a tub for accommodating the adhesive.

The coupling element 1 is furthermore provided with a recess 9, which forms the functional surface for accommodating an anti-kink device 10 (not shown in FIG. 1). Other shown functional surfaces are an installation geometry 12 for a pressure piece 13 (not shown in FIG. 1) and a positioning geometry 14 (not shown in FIG. 1). Recess 9 enables an easy and secure mounting of the anti-kink device 10 (not shown in FIG. 1), in order that such is exactly positioned. At the positioning geometry 14, the sensor is applied to a sensor holder. Another functional surface, which is utilized for the orientation of the coupling element 1 on the measuring tube, is not shown in this figure.

Figure 2:
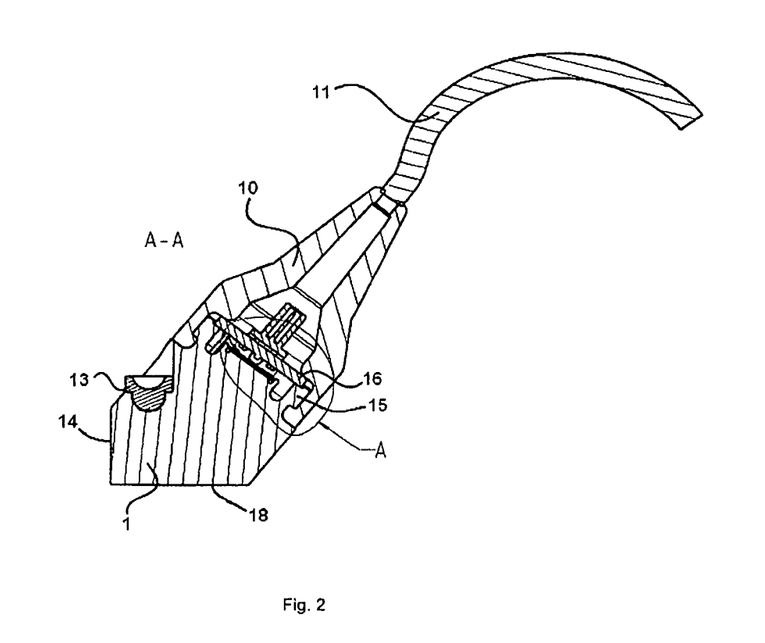
FIG. 2 is a sectional illustration of a coupling element of the invention with an anti-kink device.

FIG. 2 shows a sectional illustration of a coupling element of the invention 1 with anti-kink device 10. The anti-kink device 10 is plugged onto the coupling element 1. This anti-kink device 10 protects the cables between sensor and evaluation unit of the flow measuring device, which are led through the shielding sheath 11. The cables are connected sensor-side with the connecting circuit board 16. This connecting circuit board 16 is supported radially by a circuit board holder 17 as another functional surface and held axially tightly between anti-kink device 10 and circuit board holder 17 of the coupling element 1. The circuit board holder 17 is embodied as a shoulder of the coupling element 1. The height HH of the inner wall 15 is correspondingly greater than the height HN of the guiding elements 4 and the height HP of the pedestal 1 plus the thickness of the piezoelement 19 and possible matching, and/or adhesive, layers.

Another functional surface is a sound out- and in-coupling surface, which serves also the function of an orienting geometry 18 for the orientation of the coupling element 1 on the measuring tube. Depending on manner of construction of the coupling element 1, the orienting geometry 18 can form one functional surface with the positioning geometry 14. The pressure piece 13 is inserted into the installation geometry 12. Therewith, the coupling element 1 can be secured on, or to, a pipeline.

Figure 3:
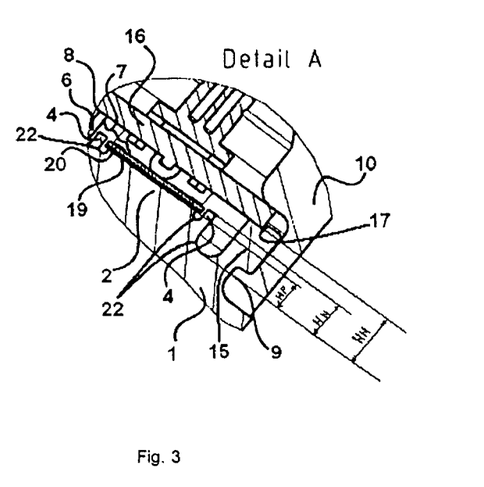
FIG. 3 is a detail view of a coupling element of the invention with an anti-kink device according to FIG. 2.

Other features of the invention are shown in the detail drawing of FIG. 3.

The connecting circuit board 16 lies in the shoulder-like circuit board holder 17 of the inner wall 15 of the coupling element 1 and is connected via a soldering 8, or riveting, with the solder pin 6, which is connected on its part via a connection cable 7 with the piezoelement 19. In this way, electrical contact between piezoelement 19 and connecting circuit board 16 is produced. The piezoelement itself is adhered via an adapting, or matching, layer 20 with the bearing surface 3 of the pedestal 2. The adapting, or matching, layer 20 has, in this drawing, approximately the same size as the piezoelement 19. Both adapting, or matching, layer 20, as well as also piezoelement 19, protrude laterally beyond the bearing surface 3 of the pedestal 2.

On the pedestal base and on the run outs of the guiding elements 4, ample radii 22 are provided, in order that no stress concentrations occur and other stresses are not introduced or forwarded to components in the immediate vicinity. The height HN of the guiding elements is greater than the height of the bearing surface HP plus the thickness of the piezoelement 19 and the thickness of the adapting, or matching, layer 20 and a thickness of the adhesive layer (not shown). The height HH of the inner wall 15 can be greater than the height of the guiding elements 4.

Figure 4:
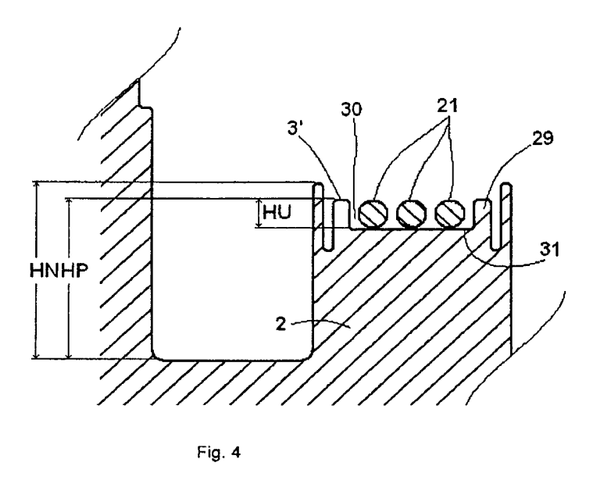
FIG. 4 is a sectional illustration of an additional coupling element of the invention.

FIG. 4 shows a detailed sectional illustration of an example of an embodiment of a coupling element of the invention. The pedestal 2 includes a tub shaped recess 30 with a surrounding rim 29 and a tub floor 31. In the tub shaped recess 30 is adhesive filled to the height of the bearing surface 3'. A braided wire 21 can likewise be inserted into the tub shaped recess. This can contribute to stability and/or be utilized for contacting the piezo. The height HU of the bearing surface 3' above the tub floor 31 amounts to preferably a fourth of the wavelength of the ultrasound in the adhesive layer, e.g. 0.2 mm, the thickness of the rim 29, for instance, half thereof, preferably 0.1 mm. An adapting, or matching, layer (not shown) can both be applied on the tub floor 31, or integrated into the tub floor 31, as well as also connected flushly and fixedly with the piezoelement 19 and, therewith, lie under the piezoelement 19, on the bearing surface 3' of the rim 29.

Figure 5:
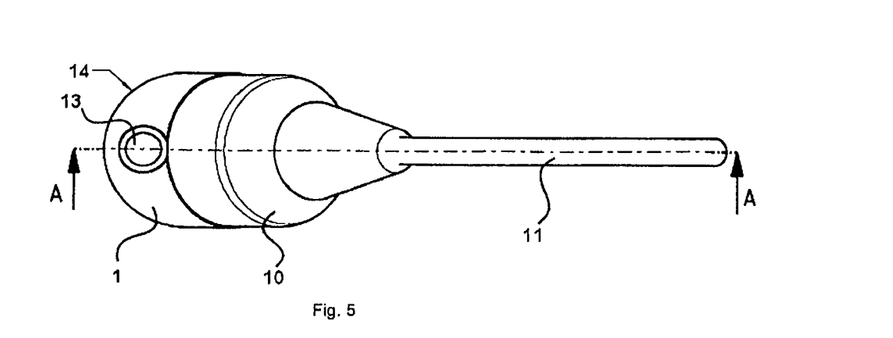
FIG. 5 shows, perspectively, a coupling element of the invention with an anti-kink device for an ultrasonic, flow measuring device according to FIG. 2.

FIG. 5 shows, perspectively, a coupling element of the invention 1 with anti-kink device 10 for an ultrasonic, flow measuring device of FIG. 2.

Figure 6:
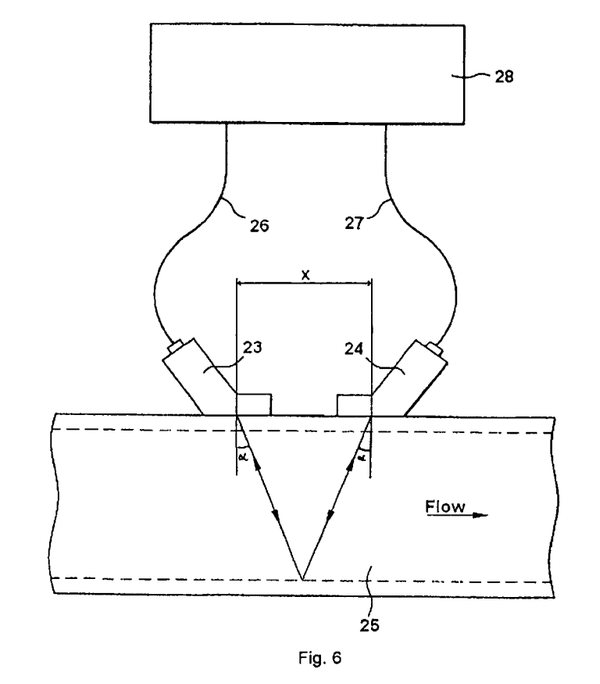
FIG. 6 is a schematic representation of a system for ultrasonic, flow measurement.

FIG. 6 shows a greatly simplified, schematic representation of a system for ultrasonic, flow measurement with two ultrasonic transducers 23, 24, which are arranged axially parallel offset from one another on the outer wall of a pipeline 25. The measured medium in the pipeline 25 flows in the direction of the arrow.

This transducer pair can be operated in two different ways. Either the ultrasonic transducer 23 acts as sending transducer and the ultrasonic transducer 24 as receiving transducer or the ultrasonic transducer 23 as receiving transducer and the ultrasonic transducer 24 as sending transducer, whereby, alternately, measurement is in the flow direction and counter to the flow direction.

Each of the ultrasonic transducers 23, 24 is composed of a coupling element 1 of the invention with piezoelement 19, which couples the ultrasonic signals at an angle $\alpha$ different from 90° either into, or out of, the wall of the pipeline 25. The angle $\alpha$ is so selected, that the signal reflected on the oppositely lying wall of the pipeline 25 hits the other ultrasonic transducer.

The piezoelements 19 transduce in such case either electrical pulses into mechanical oscillations, the actual ultrasonic signals, or, conversely, mechanical oscillations into electrical pulses.

The two ultrasonic transducers 23, 24 are each connected via connection lines 26 and 27, respectively, with a measurement circuit 28. Via these connection lines 26, 27, the electrical pulses are conveyed. Such measuring circuits 28 are known and are not subject matter of the invention.

With the coupling element of the invention, a flush bearing of the ultrasonic transducer is provided and therewith the angle relative to the pipeline very exactly determined. The separation x of the two ultrasonic transducers and the angle $\alpha$ of the signal determine essentially the accuracy of measurement of the measuring arrangement. With the coupling element of the invention, these parameters can be very precisely adjusted.

Besides the orientation of the measuring arrangement, scattering losses and reflections of the ultrasonic signal play an important role in the ultrasonic, flow measurement. Also here, a minimizing of both effects in the sensor and at its interfaces relative to the state of the art is given by the coupling element of the invention.

Figure 7:
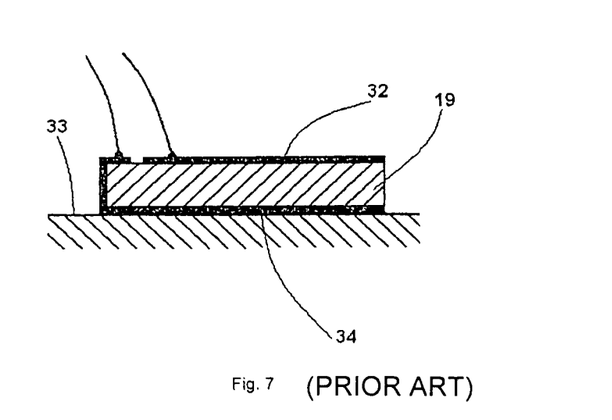
FIG. 7 shows the state of the art for contacting a flatly mounted piezoelement.

FIG. 7 shows the state of the art of the contacting of a piezoelement. With the piezoelement 19 lying flat on a bearing surface 34, the contacting of that side is not possible. Therefore, a first electrically conducting coating 32, which is applied on the side of the piezo facing away from the bearing surface, covers only a part of the piezo surface. A second electrically conducting coating 33, which is applied for the contacting of the bearing side of the piezo 19, is continuously applied to a part of the side of the piezo 19 facing away from the bearing surface. Thus, the entire piezoelement is not usable for sending and/or receiving of oscillations, but, instead only the area between both coatings. Since the so contacted piezoelement 19 is applied on the bearing surface 34 and the application is burdened with large inaccuracies in the orientation, the sound emergence, or the sound entrance, surface is not exactly determined.

Figure 8:
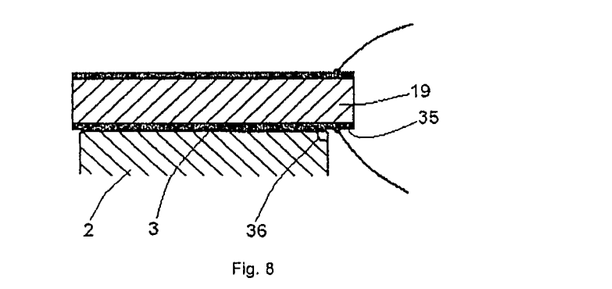
FIG. 8 is a sectional illustration of an additional coupling element of the invention.

The coupling element 1 of the invention permits by a braided wire 21 or, as shown in FIG. 8, by the projecting of the piezo 19 beyond the bearing surface, a two sided, full surface contacting of the piezo 19. According to the invention, in such case, the piezoelement 19 can have on one side of the bearing surface 3 of the pedestal 2 a greater protrusion 35 than on other sides or a cavity 36 is allowed in the pedestal 2 for the contacting of the piezo 19. The sound emergence, or sound entrance, surface is exactly determined, due to the smaller manufacturing tolerances of the pedestal 2, since the application tolerances no longer play an essential role.

The invention claimed is:

1. A coupling element for an ultrasonic, flow measuring device, having:
   a pedestal with a bearing surface; and
   a piezoelement, wherein:
   said piezoelement is applied on said bearing surface of said pedestal;
   said pedestal is an integral component of the coupling element; and
   said piezoelement protrudes beyond said bearing surface of said pedestal.

2. The coupling element for an ultrasonic, flow measuring device as claimed in claim 1, wherein:
   said pedestal has a tub shaped recess with a surrounding rim and a tub floor;
   the area of said rim facing said piezoelement forms said bearing surface, which bearing surface has a height HU relative to said tub floor; and
   said tub shaped recess is filled, at least partially, with adhesive.

3. The coupling element for an ultrasonic, flow measuring device as claimed in claim 1, further having:
   guiding elements, which are distributed around said pedestal, which have approximately equal distances to said pedestal and have approximately equal heights, wherein:
   said equal height is greater than the height of said bearing surface of said pedestal.

4. The coupling element for an ultrasonic, flow measuring device as claimed in claim 1, wherein:
   said piezoelement is electrically contacted both on the surface facing said pedestal, as well as also on the surface facing away from said pedestal, over, in each case, approximately the entire surface.

5. The coupling element for an ultrasonic, flow measuring device as claimed in claim 1, further having:
   a braided wire, or wires with approximately equal thickness, are arranged between said piezoelement and said bearing surface and/or between said piezoelement and said tub floor of said pedestal.

6. The coupling element for an ultrasonic, flow measuring device as claimed in claim 1, wherein:
   the coupling element has at least a first functional surface, by means of which a sensor holder is orientable around the coupling element, and/or by means of which the coupling element is orientable on, or with respect to, a pipeline, in which the medium to be measured flows.

7. The coupling element for an ultrasonic, flow measuring device as claimed in claim 1, further having:
   an anti-kink device, wherein:
   the coupling element has at least a second functional surface, by means of which said anti-kink device, which serves as a passageway seal for connection cables, is orientable on the coupling element for the connection cables.

8. The coupling element for an ultrasonic, flow measuring device as claimed in claim 1, wherein:
   the coupling element has at least a third functional surface, by means of which a connecting circuit board is orientable on the coupling element.

* * * * *